United States Patent
Truckai et al.

(10) Patent No.: US 11,660,467 B2
(45) Date of Patent: *May 30, 2023

(54) WEARABLE LIGHT STIMULATION SYSTEMS AND METHODS

(71) Applicant: Kemeny Healthcare Inc., San Jose, CA (US)

(72) Inventors: Csaba Truckai, Saratoga, CA (US); John H. Shadduck, Menlo Park, CA (US); Akos Toth, Cupertino, CA (US)

(73) Assignee: Kemeny Healthcare Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/811,387

(22) Filed: Jul. 8, 2022

(65) Prior Publication Data

US 2022/0347488 A1 Nov. 3, 2022

Related U.S. Application Data

(63) Continuation of application No. 17/446,703, filed on Sep. 1, 2021, now abandoned, which is a continuation of application No. 16/863,664, filed on Apr. 30, 2020, now Pat. No. 11,110,295.

(51) Int. Cl.
*A61N 5/06* (2006.01)

(52) U.S. Cl.
CPC .... *A61N 5/0616* (2013.01); *A61N 2005/0628* (2013.01); *A61N 2005/0632* (2013.01); *A61N 2005/0652* (2013.01); *A61N 2005/0659* (2013.01); *A61N 2005/0662* (2013.01)

(58) Field of Classification Search
CPC .......... A61N 5/0616; A61N 2005/0628; A61N 2005/0632; A61N 2005/0652; A61N 2005/0659; A61N 2005/0662; A61N 5/06–2005/073; A61B 18/20–18/28
USPC ..................... 607/88–94; 606/2–19
See application file for complete search history.

(56) References Cited

U.S. PATENT DOCUMENTS

| | | | |
|---|---|---|---|
| 6,241,752 B1 | 6/2001 | Sheinman et al. | |
| 6,358,272 B1 | 3/2002 | Wilden | |
| 11,110,295 B1 | 9/2021 | Truckai et al. | |
| 2004/0054386 A1 | 3/2004 | Martin et al. | |
| 2006/0282134 A1 | 12/2006 | Shapiro et al. | |
| 2012/0041523 A1* | 2/2012 | Solomon | A61N 5/0616 607/90 |
| 2013/0116612 A1* | 5/2013 | Stephan | A61F 13/00051 604/319 |
| 2013/0144357 A1 | 6/2013 | Forward | |
| 2014/0350454 A1 | 11/2014 | Klem | |
| 2016/0158486 A1 | 6/2016 | Colbaugh et al. | |
| 2019/0083809 A1* | 3/2019 | Zhang | A61N 5/0616 |
| 2020/0108268 A1 | 4/2020 | Asprey et al. | |
| 2020/0398074 A1* | 12/2020 | Lee | A61N 5/0619 |

(Continued)

OTHER PUBLICATIONS

Damber, J. "Testicular Blood Flow. Methological and functional studies in the rat," *Umea Univ Med Diss, New Series*, 39, 1-43, 1978.

(Continued)

*Primary Examiner* — Jonathan T Kuo
*Assistant Examiner* — Vynn V Huh
(74) *Attorney, Agent, or Firm* — Levine Bagade Han LLP

(57) ABSTRACT

Light stimulation systems and methods for elevating testosterone levels in male patients.

14 Claims, 6 Drawing Sheets

(56) References Cited

U.S. PATENT DOCUMENTS

2021/0015700 A1    1/2021   Truckai et al.
2021/0059896 A1    3/2021   Truckai et al.
2021/0369552 A1   12/2021   Truckai et al.
2021/0369555 A1   12/2021   Truckai et al.
2022/0143420 A1    5/2022   Truckai et al.

OTHER PUBLICATIONS

Example of fiber optic fabric used for novelty purposes: link: https://www.youtube.com/watch?v=-syaEeaTrzQ (accessed Apr. 22, 2020).

Fagiolini, A. "Lack of interest in sex successfully treated by exposure to bright light" *European College of Neuropsychopharmacology (ECNP)*; Sep. 18, 2016.

Myerson, A. et al. "Influence of ultraviolet radiation on excretion of sex hormones in the male." *Endocrinology*, 25:7-12, Jul. 1, 1939.

Wunsch, A. et al. "A Controlled Trial to Determine the Efficacy of Red and Near-Infrared Light Treatment in Patient Satisfaction, Reduction of Fine Lines, Wrinkles, Skin Roughness, and Intradermal Collagen Density Increase" *Photomed Laser Surg.*, 32(2): 93-100, Feb. 1, 2014.

\* cited by examiner

WEARABLE LIGHT STIMULATION SYSTEMS AND METHODS

CROSS-REFERENCE TO RELATED APPLICATIONS

This application is a continuation of U.S. patent application Ser. No. 17/446,703, filed Sep. 1, 2021, which is a continuation of U.S. patent application Ser. No. 16/863,664 filed Apr. 30, 2020, now U.S. Pat. No. 11,110,295, the content of each of which is incorporated herein by reference in its entirety.

FIELD OF THE INVENTION

The present invention relates to light stimulation systems and methods for elevating testosterone levels in male patients.

BACKGROUND OF THE INVENTION

Light stimulation therapy, also known as photobiomodulation (PBM), has been known for many years. As early as 1939, Dr. Myerson measured circulating testosterone in men and exposed their various body parts to UV light. After five days, testosterone levels increased by 120 percent when the light was focused on the patient's chest. Testosterone levels increased by 200% after eight days of light exposure to the patient's genitals, which reportedly was due to a boost in the production of the cells that produce testosterone (Leydig cells). Myerson, A. "Influence of ultraviolet radiation on excretion of sex hormones in the male." Endocrinology 1939; 25:7-12.

In recent years, many researchers have investigated photobiomodulation therapies, including studies using red and near-infrared light wavelengths, such as: Wunsch, A. et al. "A Controlled Trial to Determine the Efficacy of Red and Near-Infrared Light Treatment in Patient Satisfaction, Reduction of Fine Lines, Wrinkles, Skin Roughness, and Intradermal Collagen Density Increase" Photomed Laser Surg. 2014 Feb. 1; 32(2): 93-100.

Red light wavelengths are reported to stimulate the creation of ATP (adenosine triphosphate), which is involved with energy production and also boosts the activity of the Leydig cells in the testes. Such an effect may occur since red light wavelengths penetrate deeper into the skin than other visible light colors. When skin cells absorb such red light wavelengths, cell growth can greatly accelerate, which can result in collagen and elastin generation at an accelerated rate. For this major reason, therapies with red light wavelengths are frequently used to treat eczema, acne, psoriasis, and other skin disorders.

In 2016 meeting of the European College of Neuropsychopharmacology, a researcher reported on the results of a pilot trial in which 38 men with low libido were placed into one of two groups: one received bright light therapy from a light box and the other was exposed to a light box that had less bright light. The light boxes were of the type used to treat Seasonal Affective Disorder (SAD), a form of depression that responds well to such a light therapy. After two weeks of daily exposure for 30 minutes, the authors found that the testosterone levels of men who were exposed to bright light increased by 300 percent, and their libido increased by the same percentage. Fagiolini, A. "Lack of interest in sex successfully treated by exposure to bright light" European College of Neuropsychopharmacology (ECNP); Sep. 18, 2016.

SUMMARY OF THE INVENTION

The present disclosure includes methods and devices for light stimulation to a region of the body. For example, such light stimulation can enhance testosterone levels in a patient when the stimulation is applied to the patient's testes.

A method under the present disclosure includes positioning a wearable structure carrying light emitters proximate to testes of a patient, where the wearable structure carrying light emitters emits at least one selected wavelength between 400 nm and 850 nm; actuating the light emitters in a duty cycle consisting of an ON/OFF sequence wherein the ON interval totals at least 5 minutes in at least a 30 minute period; and providing an irradiance in the range of 20 mW/cm2 to 200 mW/cm2 to the patient's testes where such irradiance enhances testosterone levels in the patient.

The present disclosure also includes light stimulation systems comprising a structure carrying at least one light emitter configured to emit at least one selected wavelength between 400 nm and 850 nm, wherein the at least one light emitter is adapted for carrying in a wearable garment configured to position the at least one light emitter proximate to testes of a patient; and a controller configured to activate the at least one light emitter to provide a selected irradiance in a duty cycle consisting of an ON/OFF sequence wherein the ON interval totals at least 5 minutes per hour over at least a 2 hour period.

The light stimulation described herein can include irradiance ranges from 50 mW/cm2 to 150 mW/cm2 or from 80 mW/cm2 to 120 mW/cm2.

Variations of the method and systems described herein can employ light emitters that comprise LEDs carried in a substrate. Alternatively, or in combination, other light sources can be used. In additional variations, the light emitters comprise side-emitting optical fibers carried in a fabric. For example, side-emitting optical fibers can be detachably coupled to at least one LED. Any combination of light emitting devices can be combined in a device under the present disclosure.

In variations of the device, the fabric can be separate from the wearable structure. Alternatively, the fabric can be integrated in the wearable structure.

The methods and devices described herein can include a controller to modulate operating parameters of the light emitters. For example, actuating the light emitters includes using the controller to control the irradiance in a duty cycle consisting of an ON/OFF sequence wherein the ON intervals total at least 5 minutes over at least a 30 minute period.

In another variation, the methods and/or devices can include an ON/OFF sequence having an ON interval ranging from 1 millisecond to 30 minutes and an OFF interval ranging from 1 millisecond to 10 minutes.

Additional variations include a temperature sensor coupled to the structure. The controller can modulate operating parameters of the light emitters in response to signals from a temperature sensor. Such operating parameters can include (i) at least one selected wavelength, (ii) irradiance, and (iii) duty cycle.

In an additional variation, the methods and systems can further include connecting the light emitters to a wearable module carrying a controller and a power source.

The systems and methods described herein can include light emitters comprising an array of 2 to 200 LEDs. The array can be carried by a flexible substrate.

The methods and systems can further include a cooling mechanism configured to be carried by the wearable garment and comprising at least one of a Peltier element, a flat flexible polymer heat pipe and a heat sink element. In additional variations, the systems and methods include a sensing mechanism configured to be carried by the wearable garment and selected from the group of pulse oximeters, impedance sensors and capacitance sensors.

In yet an additional variation, the light emitters are spaced apart from a perimeter of the device by at least 5 mm.

BRIEF DESCRIPTIONS OF THE DRAWINGS

The present invention will be more fully appreciated and understood from the following detailed description of the present invention when viewed in conjunction with the accompanying figures.

DETAILED DESCRIPTION OF THE INVENTION

The following detailed description describes currently contemplated modes of carrying out the invention. The description is not limiting but is made for the purpose of illustrating the general principles of the invention.

Figure 1:
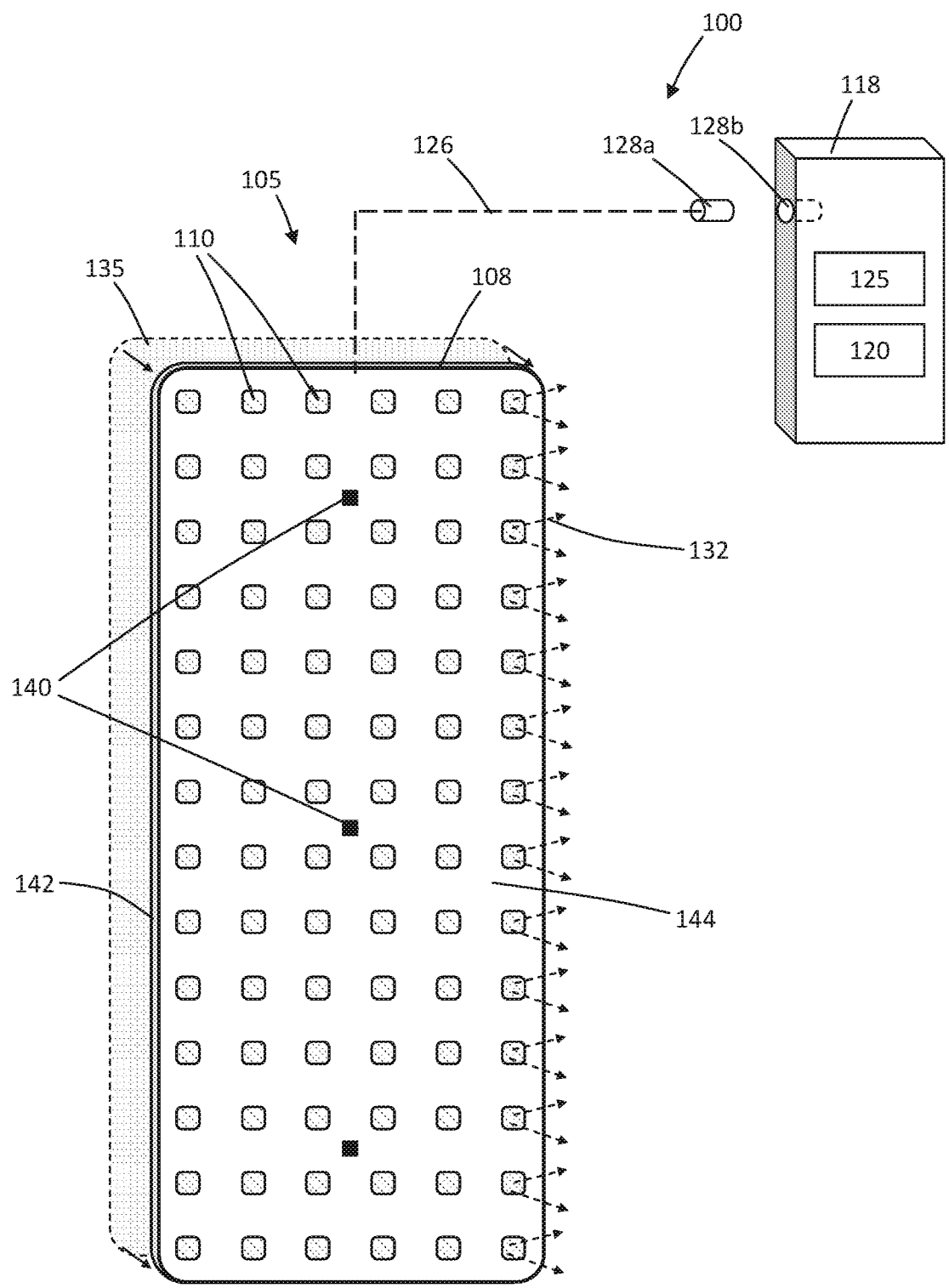
FIG. 1 is an illustration of a light stimulation device comprising a flexible substrate carrying a plurality of LEDs having a selected wavelength for light stimulation of a patient's testes, wherein the substrate is shaped and configured for positioning and wearing in an underwear-type garment and the device is operatively connected to a wearable module carrying a controller and power source.

FIG. 1 illustrates a light stimulation system 100 for providing a photobiomodulation (PBM) therapy to elevate testosterone levels in a male patient. The system 100 includes a device 105 comprising a substrate 108 carrying a plurality or array of LED light emitters 110 that are adapted to irradiate a male patient's genitals 111 and more particularly the patient's testes 112 (see FIG. 2). The substrate 108 can be designed to have varying levels of flexibility. In additional variations, the substrate can be rigid.

Figure 2:
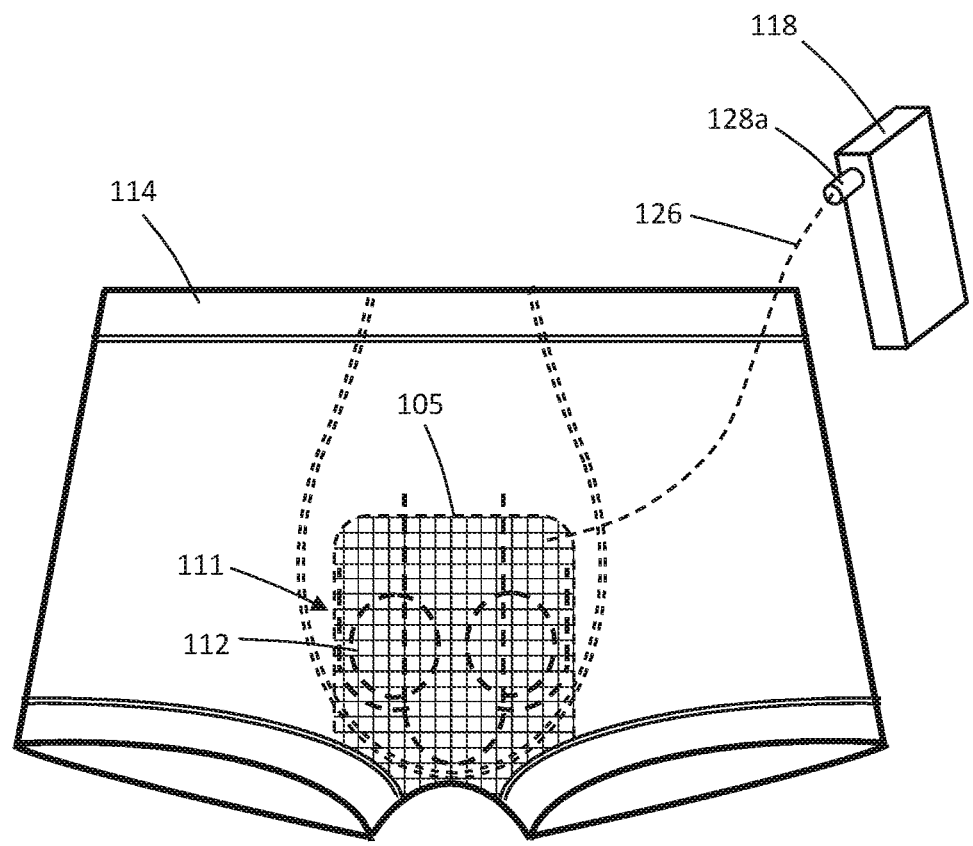
FIG. 2 is a schematic view of a substrate of FIG. 1 carried in a garment.

The testes are the body's main source of male hormones such as testosterone, and light stimulation is adapted to increase testosterone levels. Referring to FIG. 2, a flexible substrate 108 carries the LEDs 110 and is shaped and configured to be positioned proximate to the patient's genitals 111 and testes 112 by being carried within an underwear-type garment 114, which can take any form, such as conventional briefs or a specially made undergarment. Additional variations of the device can be positioned in any type of garment. As can be seen in FIG. 1, the flexible substrate 108 and LEDs 110 are operatively coupled to a portable module 118 which carries a power source 120 (e.g., a battery) for energizing the LEDs 110 and a processor or controller 125 for controlling operating parameters of the LEDs. The battery can be a rechargeable lithium battery with low voltage that allows for USB charging or the like.

As can be seen in FIGS. 1 and 2, the LEDs 110 are detachably connected to the module 118 by an electrical cable 126 with a first connector 128a that cooperates with a second connector 128b in the module 118. The module 118 is adapted to be carried by, or worn by, the patient and can be configured with belt loops, can be carried by velcro attachment to a garment, can be carried within a pocket in an undergarment, or carried in a pocket in an outer garment.

As can be understood from FIG. 1, light is emitted from the LEDs in expanding light beams 132 that propagate generally perpendicularly to the plane of the flexible substrate 108. The array of light LED emitters 110 can comprise from 2 to 200 LEDs. In one variation, the LEDs emit at least one selected wavelength that ranges between 400 nm and 850 nm. The controller 125 is configured to activate or actuate the LEDs 110 to provide a selected irradiance described below in a duty cycle consisting of an ON/OFF sequence wherein the ON interval totals at least 5 minutes over at least a 30 minute period, and often 10 minutes per hour over at least a 1 hour period. In a variation, the LEDs operate to provide an irradiance that ranges from 20 mW/cm$^2$ to 200 mW/cm$^2$. Often, the irradiance is from 50 mW/cm$^2$ to 150 mW/cm$^2$ or from 80 mW/cm$^2$ to 120 mW/cm$^2$.

In a variation, the controller 125 carried by the system 100 includes algorithms for modulating operating parameters of the system 100, where the parameters consist of (i) at least one selected wavelength, (ii) irradiance, and (iii) duty cycle. The device 105 can carry a plurality of LEDs wherein the various LEDs have different wavelengths or alternatively the device can carry a plurality of LEDs that provide varied different wavelengths. The controller 125 further can selectively modulate the selected wavelengths over a treatment interval to thus provide a polychromatic photobiomodulation therapy. The controller 125 can also modulate the irradiance over the time of a treatment interval, wherein the varied irradiance can be within the range described above, e.g., an irradiance range from 20 mW/cm$^2$ to 200 mW/cm$^2$. In a variation, the controller 125 also can modulate the duty cycle, wherein the ON/OFF sequence includes an ON interval ranging from 1 millisecond to 30 minutes and an OFF interval ranging from 1 millisecond to 10 minutes In another variation, still referring to FIG. 1, the device 105 can carry at least one temperature sensor 140 carried in the substrate 108 (e.g., a surface or within the surface), which is adapted to send temperature signals to the controller 125. In this variation, the controller 125 can further include algorithms adapted to modulate the operating parameters of the LEDs, (i.e., (i) selected wavelength, (ii) irradiance, (iii) duty cycle) in a feedback mode that is responsive to the temperature signals from the sensor 140. The temperature sensor can comprise any form of temperature sensing mechanism, such as a thermistor, a positive temperature coefficient (PTC) resettable switch, a thermocouple, negative temperature coefficient (NTC) or the like. In other variations, the device 105 can carry one or more other sensing mechanisms for sensing environmental or patient conditions at the treatment site and sending signals to the controller 125 which then allows for feedback control of the operating parameters of the system. Such alternative a sensing mechanism can be carried by the device 105 or the wearable garment 114 (FIG. 2) and include of pulse oximeters, impedance sensors and capacitance sensors.

Referring to FIG. 1, the device 105 also may be configured with a thin film reflective layer 135, such as mylar, on the back side 142 of the substrate 108 that opposes the front side 144 of the device which emits light to the patient. In general, the reflective material is adapted to reflect light emitter by the LEDS toward the targeted site in the patient.

Figure 3:
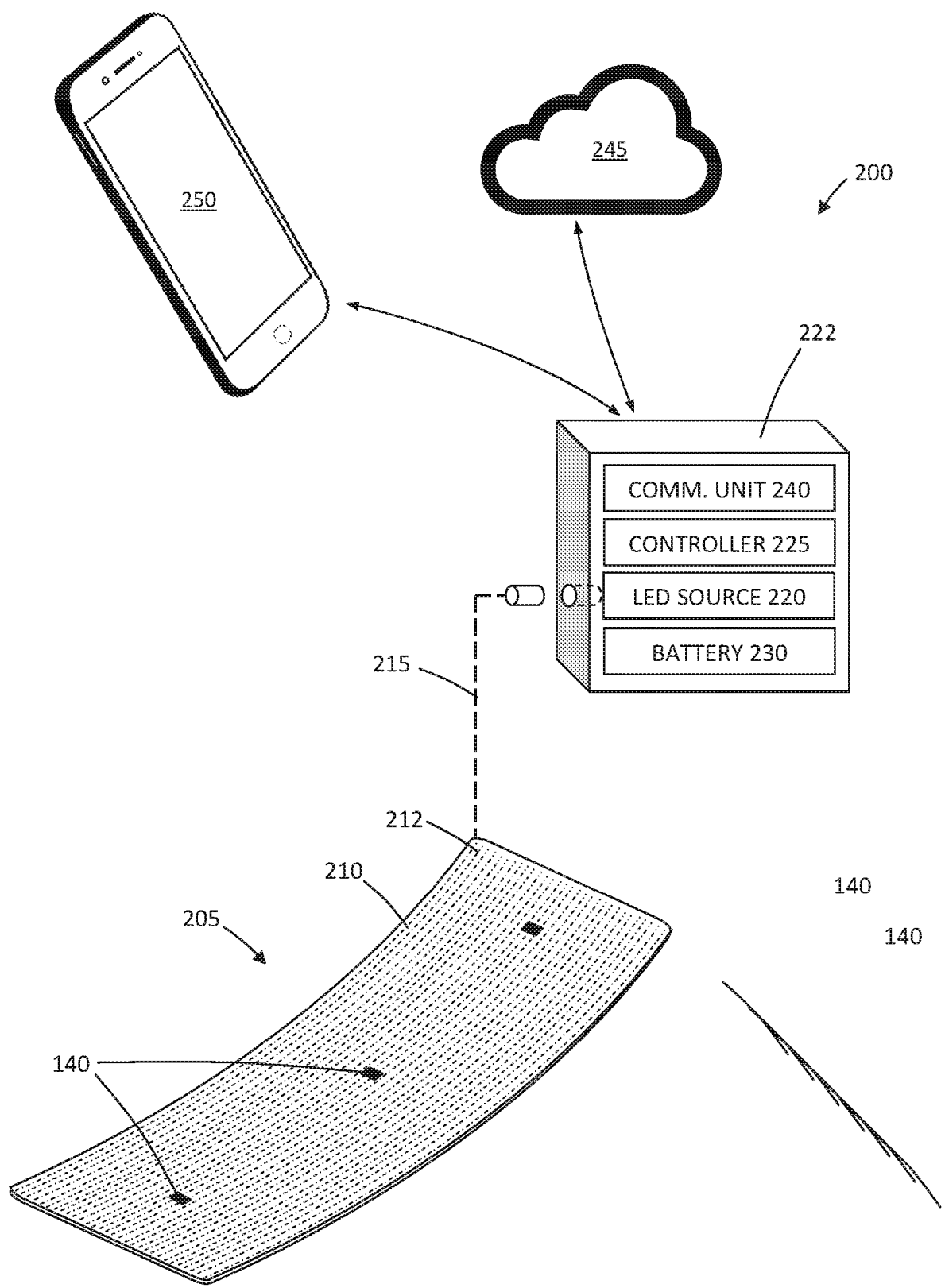
FIG. 3 is an illustration of another variation of a light stimulation device comprising a fabric with side-emitting optical fibers integrated into the fabric, wherein the fabric is shaped and configured for positioning and wearing in the underwear-type garment as in FIG. 2, and where the fabric device is operatively connected to a wearable module carrying a controller and power source.
Figure 4:
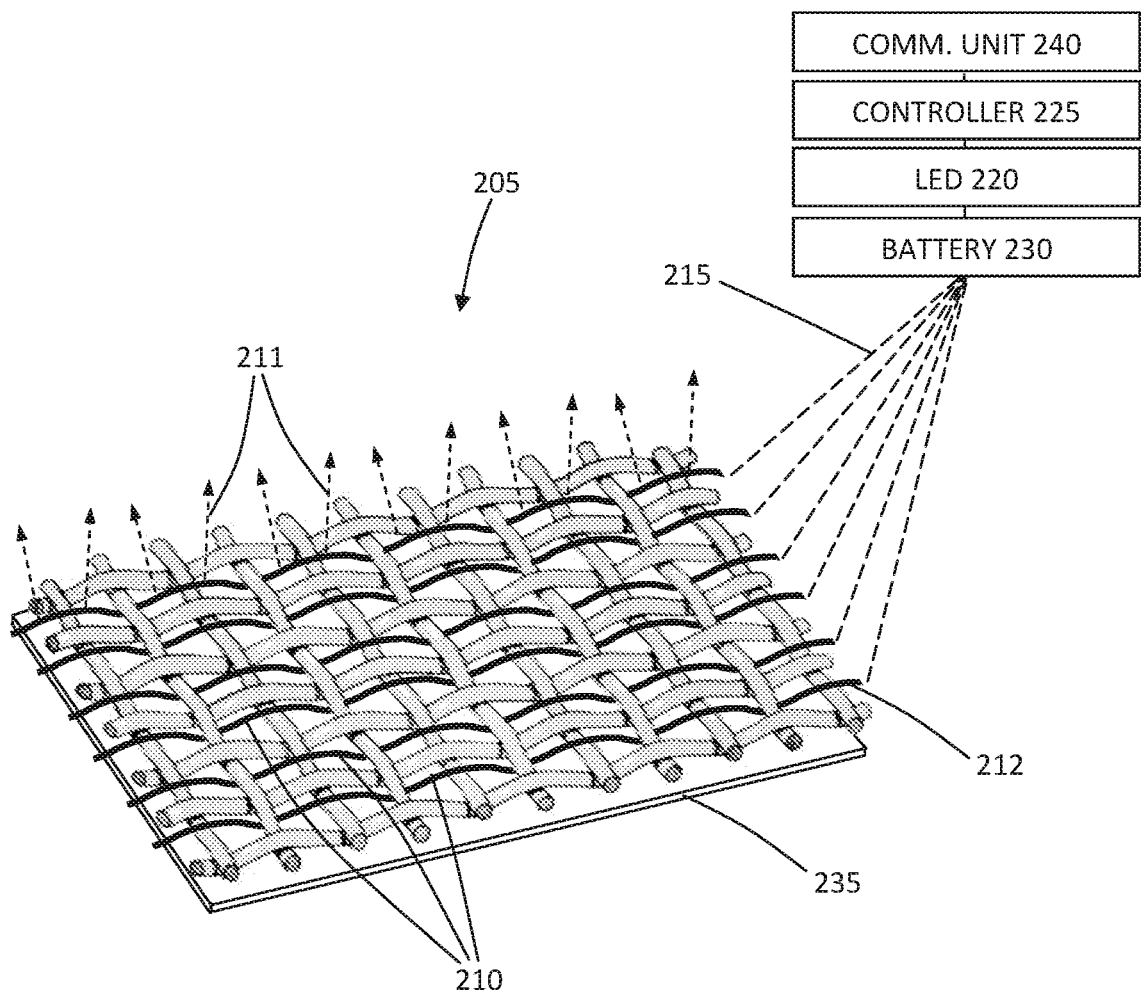
FIG. 4 is a greatly enlarged view of a portion of the fabric device of FIG. 3 showing the side-emitting optical fibers integrated with the woven fabric.

Now turning to FIG. 3, in another variation, light stimulation device 200 of the invention comprises a light-emitting fabric member 205 that is adapted for positioning in the patient's underwear-type garment 114 as shown in FIG. 2. In this variation, the fabric member 205 can consist of any woven, knit, braided, or entangled threads together with side-emitting optical fibers 210 integrated therein, as shown schematically in FIG. 4. The optical fibers 210 are processed so that the surface cladding allows light to be emitted or diffused in emissions indicated at 211 along the full length of the fibers, hence the term "side-emitting" optical fibers. The fabric member 205 is similar to any synthetic fabric as it can be sewn and washed. In general, the optical fibers 210 are arranged and distributed in the fabric member 205 to be parallel with one another. The fibers have a small diameter, for example from 100 μm to 500 μm. Typically, the optical fibers 210 are distributed evenly across the width of the fabric member 205, but such fibers 210 also may be integrated into the fabric member in different densities or patterns to focus light emissions. The proximal ends 212 of the optical fibers 210 are collected into a fiber-optic bundle or cable 215 that can be detachably connected to the LED light source 220 in a wearable module 222 (see FIG. 3) similar to that described previously. In this variation, the module 222 carries a controller 225 and battery 230 that are similar to the previous embodiment. In another variation, as illustrated in FIG. 4, the fabric member 205 can also carry a thin-film reflective layer 235 (e.g., mylar film) as described previously that is configured to reflect light toward the patient. The reflective layer 235 is useful since the side-emitting fibers 210 generally emit light in all directions around each fiber.

In one variation shown in FIG. 3, the system 200 further includes a communication unit 240 configured to function as a wireless link that is adapted to send and receive data from the cloud 245 or from an alternative memory unit for storing and analyzing patient and user data. The communication unit 240 also is adapted to communicate with a touchscreen 250 or other means for monitoring, adjusting and controlling all operating parameters of the system 200. The wireless link to the cloud 245, the tablet or the phone 250 can be used for monitoring patient compliance, for data collection, or for remote adjustment of operating parameters of the system 200.

In general, a light stimulation method corresponding to the invention comprises (i) providing a wearable structure carrying light emitters that emit at least one selected wavelength between 400 nm and 850 nm, wherein the light emitters are positioned in the wearable structure to be proximate to testes of a patient, (ii) actuating the light emitters in a duty cycle consisting of an ON/OFF sequence wherein the ON interval totals at least 5 minutes per hour over at least a 2 hour period, and (iii) providing an irradiance in the range of 20 mW/cm$^2$ to 200 mW/cm$^2$ to the patient's testes to thereby enhance testosterone levels in the patient. Often, the method provides an irradiance ranging from 50 mW/cm$^2$ to 150 mW/cm$^2$ or from 80 mW/cm$^2$ to 120 mW/cm$^2$ In another variation, the system allows for recording of a patient's treatment in terms of operating parameters. In a typical form of treatment, the system is adapted for personal use under a physician's care wherein the stored data then can be reviewed by the physician for patient compliance with the treatment program. Typically, a patient will wear the garment and light stimulation device for treatments period which may be from 1 weeks to 6 months. In some variations, the light stimulation may be used indefinitely as a maintenance therapy to maintain testosterone levels at a selected level. As described above, the system can include a module for uploading the treatment data to the cloud 245 which then can be reviewed by the physician for compliance.

Figure 5:
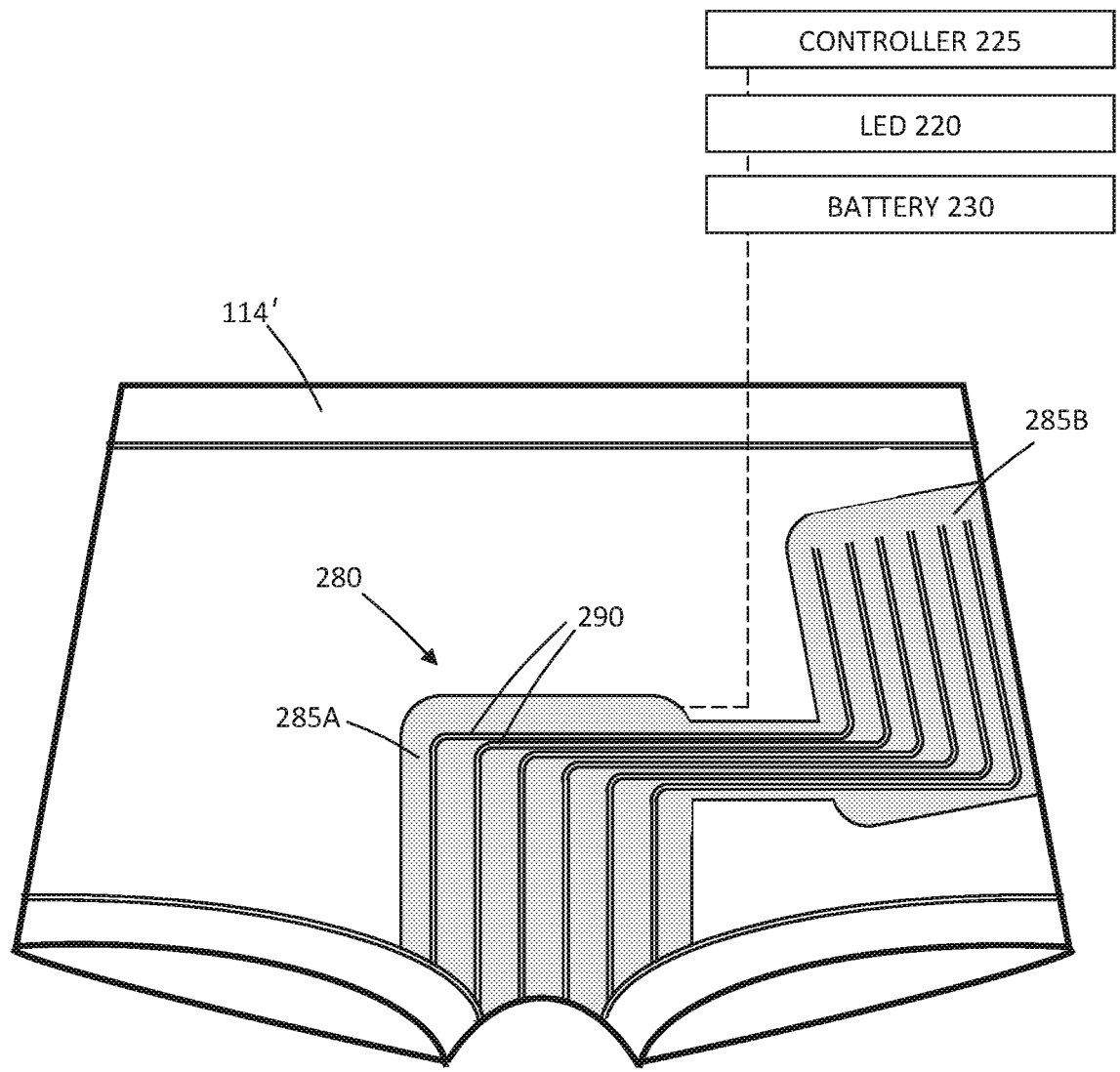
FIG. 5 is another variation of a light stimulation device similar to that of FIGS. 1 to 4 that carries a cooling mechanism.

In another variation, the light stimulation systems 100 and 200 of FIGS. 1, 2 and 3 can further include a cooling mechanism carried by the wearable device 105, 205 or the garment 114 (FIG. 2) comprising at least one of flat flexible polymer heat pipes, heat sink elements or flexible thermo-electric (Peltier) elements (see FIG. 5). While the irradiance levels described above are configured to generate little to no heat, or use temperature-responsive feedback control, some system embodiments may benefit from a passive or an active cooling mechanism. FIG. 5 is a schematic view of a system with a passive cooling mechanism where the light emitter device 280 that has a light-emitting LEDs or fibers in a first portion 285A that is similar to the devices 105 and 205 of FIGS. 1 and 3 above. In addition, the device 280 can have a second portion 285B adapted for dissipating heat transferred from the light-emitting portion 285A. In this embodiment, heat sink or heat transfer elements 290 are shown in FIG. 5, which can be heat conductors (e.g., copper elements, flat flexible polymer heat pipes, or the like. In one variation, the second portion 285B can be disposed in a region of the garment 114' spaced apart from the treatment site.

Figure 6:
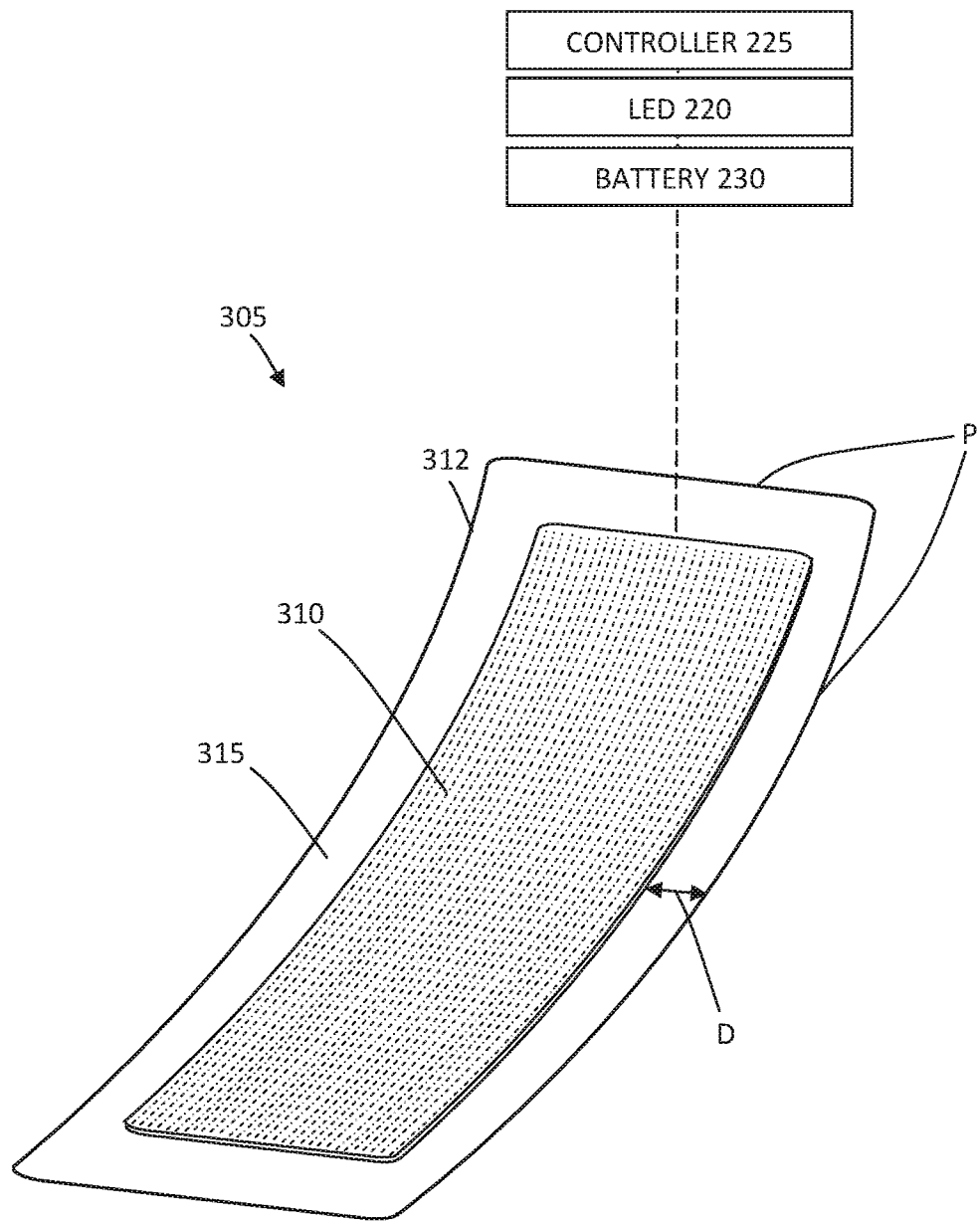
FIG. 6 is another variation of a light stimulation device similar to that of FIGS. 1 to 4 that has an edge or skirt around at least portions of the device to substantially prevent light emissions around the edge of the device.

Referring to FIG. 6, another variation of a device 305 similar to the light stimulation systems 100 and 200 of FIGS. 1 and 3 is configured with the LEDs or light emitting fibers 310 being positioned inwardly a distance D of at least 5 mm and often at least 10 mm from edges 312 of the device 305. In other words, the substrate of material of the device 305 is configured with a skirt portion 315 that is not light transmissible which is adapted to prevent light from propagating outside the perimeter P of the device. The skirt portion thus prevents any light being visible during use through the user's clothing.

In another variation, a light emitting device 105 or 205 as shown in FIGS. 1 and 3 can be adapted to provide a self-disinfecting mode of operation, where LEDs emit UV radiation that can reduce or eliminate biological contamination on the device. In this variation, the controller would include an algorithm for activating a selected cycle of UV radiation after an interval of light stimulation. Such a UV light cycle could be performed while the patient was wearing the garment. In another variation, the UV light cycle could be performed with the light stimulation device disposed within an enclosure (e.g., a bag, pouch, box, container, etc.) after being worn by the patient. Such an enclosure can include reflective interior surfaces to cause the UV radiation to irradiate all surfaces of the device effectively. In another variation, the light emitting device 105 or 205 of FIGS. 1 and 3 can be configured with LEDs capable of increasing the temperature of the device to disinfect surfaces of the device. Such elevated temperatures can be controlled by the controller and used in conjunction with, or independent of, UV irradiance as a disinfecting mechanism. In these variations, the device 105 or 205 of FIGS. 1 and 3 also can include sensors in the device that monitor the UV light emitted and/or the device temperature to modulate energy delivery based on feedback from the sensors to assure that the device has been treated sufficiently to disinfect the surfaces of the device.

In another variation, the wearable device 105 or 205 of FIGS. 1 and 3 can have a curved shape, a pouch shape or any suitable shape for conforming to the patient's body. In a variation, device can be shapeable to the user's anatomy, and can carry a layer of uncured material (e.g., a resin, gel, etc.) that can be exposed to oxygen and/or moisture from the air which can set the material of the device into a permanent shape. In a variation, the material can be set into a selected final shape by the light wavelengths emitted by LEDs carried by the device, such as UV irradiation. In another variation, a light emitting facemask can use a similar material that can be shaped to a particular patient's face and then cured to the custom selected shape.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A light stimulation method for providing irradiance therapy to an individual's testes to enhance testosterone levels in the individual, the method comprising: positioning a wearable structure carrying a plurality of light emitters proximate to testes of a patient, wherein the plurality of light emitters are configured to emit at least one selected wavelength between 400 nm and 850 nm; actuating a controller configured to activate the plurality of light emitters to provide a selected irradiance in a duty cycle consisting of an ON and OFF sequence comprising ON and OFF intervals; modulating the duty cycle in response to signals from at least one temperature sensor in the structure indicating a selected temperature at which to modulate the irradiance; cooling the wearable structure with a cooling mechanism carried within the wearable structure, wherein the cooling mechanism dissipates heat transferred from the plurality of light emitters proximate to the testes of the patient while the wearable structure is worn by the patient; and providing the irradiance in a range between 20 mW/cm$^2$ to 200 mW/cm$^2$ to the patient's testes where such irradiance enhances testosterone levels in the patient.

2. The light stimulation method of claim 1, wherein the ON intervals total at least 5 minutes over at least a 30 minute period.

3. The light stimulation method of claim 1, wherein the ON intervals total at least 5 minutes per hour over at least a 2 hour period.

4. The light stimulation method of claim 1, wherein the ON intervals total 10 minutes per hour over at least a 1 hour period.

5. The light stimulation method of claim 1, wherein the plurality of light emitters comprise LEDs carried in a substrate.

6. The light stimulation method of claim 1, wherein the plurality of light emitters comprise side-emitting optical fibers carried in a fabric.

7. The light stimulation method of claim 6, wherein the side-emitting optical fibers are detachably coupled to at least one LED.

8. The light stimulation method of claim 6, wherein the fabric is separate from the wearable structure.

9. The light stimulation method of claim 6, wherein the fabric is integrated in the wearable structure.

10. The light stimulation method of claim 1, wherein the ON interval ranges from 1 millisecond to 30 minutes and the OFF interval ranges from 1 millisecond to 10 minutes.

11. The light stimulation method of claim 1, further comprising utilizing the controller to modulate operating parameters of the plurality of light emitters, wherein the operating parameters include (i) the at least one selected wavelength, (ii) the irradiance, and (iii) the duty cycle.

12. The light stimulation method of claim 1, further comprising connecting the plurality of light emitters to a wearable module carrying the controller and a power source.

13. The light stimulation method of claim 1, further comprising reflecting light emitted by the plurality of light emitters toward the testes of the patient with a reflective layer on the wearable structure.

14. The light stimulation method of claim 1, wherein the cooling mechanism comprises at least one of heat pipes, heat sink elements, or flexible thermoelectric elements.

\* \* \* \* \*